United States Patent [19]

Isami et al.

[11] Patent Number: 5,374,398
[45] Date of Patent: Dec. 20, 1994

[54] APPARATUS FOR ANALYZING PARTICLES

[75] Inventors: Yasushi Isami, Himejishi; Naomiki Kojou, Kobe, both of Japan

[73] Assignee: Toa Medical Electronics Co., Ltd., Kobe, Japan

[21] Appl. No.: 821,035

[22] Filed: Jan. 16, 1992

[30] Foreign Application Priority Data

Apr. 5, 1991 [JP] Japan .................................. 3-102116

[51] Int. Cl.$^5$ ...................... G01N 21/05; G01N 21/53
[52] U.S. Cl. ..................................... 422/81; 422/82.05;
422/111; 356/73; 137/88; 73/863.03
[58] Field of Search .................. 356/72, 73, 39; 137/3,
137/88, 101.21; 422/63, 67, 68.1, 82.05, 73, 81,
111, 119; 250/461.2, 461.1; 73/861.01, 863.03,
864.81, 863.01

[56] References Cited

U.S. PATENT DOCUMENTS

| | | | |
|---|---|---|---|
| 4,683,212 | 7/1987 | Uffenheimer | 356/73 X |
| 4,896,961 | 1/1990 | Ito | 356/73 |
| 5,030,002 | 7/1991 | North, Jr. | 356/336 X |
| 5,040,890 | 8/1991 | North, Jr. | 356/73 X |

OTHER PUBLICATIONS

Perry, R. H. et al. "Perry's Chemical Engineers' Handbook" 6th ed., New York, McGraw-Hill Book Co., 1984, pp. 5/27–5/28.

Primary Examiner—Jeffrey R. Snay
Attorney, Agent, or Firm—Jones, Tullar & Cooper

[57] ABSTRACT

An apparatus for analyzing particles in a sample liquid which classifies or counts components in the sample liquid by image processing. The liquid sample can be urine or the like and is passed in a flattened flow. The apparatus comprises sheath liquid supply apparatus sample liquid discharge apparatus a, temperature sensor for detecting the ambient temperature and temperature measuring circuit for measuring the temperature depending on the output of the temperature sensor, and a driving circuit for driving the sample liquid discharge apparatus by correcting the sample liquid discharge flow rate depending on the signal from the temperature measuring circuit. The sheath liquid is supplied at a specific pressure, and the sample liquid discharge quantity is corrected depending on the ambient temperature. When changed to the high scale factor taking state or low scale factor taking state, a different correction rate is set. Thus, if the environmental conditions such as temperature should vary, the sample liquid volume is kept constant, so that particles may be analyzed at high precision.

2 Claims, 9 Drawing Sheets

(HIGH TEMP. CASE)

APPARATUS FOR ANALYZING PARTICLES

BACKGROUND OF THE INVENTION

The present invention relates to a method and apparatus for analyzing particles by passing a sample liquid such as urine taken from a subject in a flattened flow, and classifying or counting visible components in the sample liquid by processing the image.

An apparatus is known for taking cells or particles in a flat sheath flow by a video camera, and classifying or counting the particles by image processing. A flat sheath flow passes a particle suspension by covering or surrounding it with a laminar flow liquid. The particle suspension is formed in a flattened flow with a large slenderness ratio.

FIG. 1 is a schematic diagram of such an apparatus, which is intended to analyze components (blood cells, epithelial cells, cylinders, etc.) in a urine sample. The urine sample which is pretreated by dyeing or the like is discharged from a nozzle 12 rate by sample liquid discharge means 18 at a specific flow rate, and is led into a flat sheath flow cell 10. At the same time, in the flow cell 10, a sheath liquid is also fed in by sheath liquid feed means 21, and an extremely flat (thin and broad) sample liquid flow is formed in a rectangular passage 14 with a section having a large slenderness ratio. The sheath liquid is fed by a pump 22 through a sheath liquid chamber 20 (a syringe may be used for feeding the sheath liquid, but the cost is higher). The sample liquid discharge means 18 is a syringe type driven, for example, by a motor 19.

From one side across the rectangular passage 14 (from the back side of the sheet of paper in FIG. 1), a strobe is emitted, and a still image of the sample liquid is taken by a video camera disposed on the other side (not shown). Numeral 16 is a part where an objective lens (not shown) is disposed. The picture which is taken is analyzed by an image processor, and the cell images are drawn, and particles are classified and counted.

When ambient temperature changes, the viscosity of a fluid varies, which affects the liquid flow. In a system where the sheath liquid is supplied at a specific pressure, the flow rate of the sheath liquid varies due to a change in fluid resistance, and the balance of the flow rate of sample liquid and sheath liquid is broken. When the temperature becomes higher, the flow rate increases abruptly.

FIG. 2 to FIG. 5 will be used to explain the flow of sample liquid in the flat sheath flow cell 10. FIG. 2 and FIG. 4 are front views, FIG. 3 is a sectional view of line 3—3 in FIG. 2, and FIG. 5 is a sectional view of line 5—5 in FIG. 4. Numeral 26 shows a sample liquid flow part. Numeral 28 is a video camera taking area.

At low temperature, the viscosity of the liquid (the sheath liquid in this case) is high, the flow rate of the sheath liquid is low, the sample liquid flows in a broad width W1 and a great thickness D1 as shown in FIGS. 2, 3. At high temperature, on the contrary, as shown in FIGS. 4, 5, the sample liquid flows in a narrow width W2 and a small thickness D2.

On the other hand, the taking area 28 is not changed. Therefore, a difference is caused in the volume of the sample liquid that can be taken in the entire sample liquid, which may affect the results of the analysis. For example, the number of taken particles differs.

The ordinate axis of in FIG. 6 denotes the changing rate of the number of taken particles, and the abscissa axis represents the liquid temperature. The peformance is based on the liquid temperature of 24° C. The solid line indicates the change of the number of taken particles in the conventional apparatus, in which the number of taken particles is larger at low temperature, and smaller at high temperature.

In an ordinary flow cytometer, on the other hand, when supplying the sheath liquid at a specific pressure, the thickness of the sample liquid flow varies similarly. As shown in FIG. 7, however, light 30 is emitted by completely crossing the sample liquid flow 32, and the entire sample liquid flow can be detected. Therefore, if the temperature fluctuates, only the frequency band of the particle signals changes somewhat due to flow rate changes of the sample liquid, and serious problems such as change in counting due to change of sample liquid volume to be detected can be avoided.

Thus, in an apparatus design to detect a part, not all, of a sample liquid flow, it is very important to eliminate the fluctuations of flow due to temperature variations.

To solve this problem, for example, in the sheath liquid piping 24 shown in FIG. 1,
  (a) a thermostatic unit may be disposed, or
  (b) flow rate detecting means may be provided to control the pump pressure.

In the case of (a), a heater or a cooler and its temperature control means are needed, which results in a cost increase and size of the apparatus. Practically, a block of high thermal conductivity in which a flow passage is formed is necessary, and in order to keep this block at a constant temperature, a heater of a larger thermal capacity is required.

In the case of (b), flow rate detecting means and pump output pressure control means are necessary, and the cost is similarly raised. Besides it is difficult to control the pump output pressure precisely.

OBJECTS AND SUMMARY OF THE INVENTION

It is hence a primary object of the invention to provide a method and apparatus for analyzing particles capable of being analyzing at high precision while keeping constant the width and thickness of the flow of sample, regardless of changes of ambient conditions such as temperature, without increasing the cost or size of the apparatus.

To achieve the above object, as evident from a comparison of FIGS. 1 and 8, the apparatus for analyzing particles of the invention comprises, among others, a temperature sensor for detecting the ambient temperature and a temperature measuring circuit for measuring the temperature on the basis of changes of the temperature sensor, in which driving of the sample liquid discharge means is controlled on the basis of the signal from the temperature measuring circuit by a driving circuit of the sample liquid discharge means.

More specifically, the invention provides an apparatus for analyzing particles by emitting a strobe light to sample flow in an extremely flattened flow condition having a sheath liquid as an outer layer to obtain a still picture, and analyzing components in the sample liquid by image processing, in which the sheath liquid is supplied at a specific pressure, and the discharge flow rate of the sample liquid discharge means is variable. The apparatus further comprises a temperature sensor for detecting the ambient temeprature, a temperature measuring circuit for measuring the temperature on the basis of the changes of the temperatures sensor, and a driving circuit for driving the sample liquid discharge means so that the discharge flow rate of the sample liquid discharge means may agree with a specific value depending on the signal from the temperature measuring circuit.

In the driving circuit, data for defining the relationship between the temperature information and the operating speed of the sample liquid discharge means is prepared, and the operating speed of the sample liquid discharge means is determined from the temperature information and the data.

In an apparatus designed to photograph the same sample liquid by varying in the process the taking scale factor the same correction cannot be done because the taking area and the other conditions are different. That is, data for a low scale factor and data for a high scale factor are prepared.

The invention provides a method for analyzing particles by emitting a strobe light to a sample flow in an extremely flattened flow condition, having a sheath liquid as an outer layer to obtain a still picture, and analyzing components in the sample liquid by image processing, wherein the sheath liquid is supplied at a specific pressure, and the sample liquid discharge flow rate is corrected depending on the ambient temperature.

The invention also provides a method for analyzing particles by emitting a strobe light to a sample flow in an extremely flattened flow conditions, having a sheath liquid as an outer layer to obtain the still picture, and analyzing components in the sample liquid by image processing, wherein in a same sample liquid, either the low scale factor taking state for simultaneously selecting the states of (a), (c), and (e), that is, (a) the state of reducing the quantity of light emitted to the region where the sample liquid flows, (c) the state of passing the sample liquid by increasing its thickness, and (e) the state of taking the still picture of the sample liquid at a low scale factor, or the high scale factor taking state for simultaneously selecting the states of (b), (d), and (f), that is, (b) the state of increasing the quantity of light, (d) the state of passing by reducing the thickness, and (f) the state of taking the picture at a high scale factor is selected, and the sheath liquid is supplied at a specific pressure, the discharge flow rate of the sample liquid discharge means is controlled, and the correction factor is changed whether in the high scale factor taking state or in the low scale factor taking state when correcting the sample liquid discharge flow rate depending on the ambient temperature.

The invention further provides an apparatus for analyzing particles by emitting a strobe light to a sample flow in an extremely flattened flow condition, having a sheath liquid as an outer layer to obtain a still picture, and analyzing components in the sample liquid by image processing, comprising:

sheath liquid supply means for supplying a sheath liquid at a specific pressure, sample liquid discharge means capable of controlling the discharge flow rate, a temperature sensor for detecting the ambient temperature, a temperature measuring circuit for measuring the temperature on the basis of the changes of the temperature sensor, and a driving circuit for driving the sample liquid discharge means by correcting the discharge flow rate of the sample liquid discharge means depending on the signal from the temperature measuring circuit.

The invention moreover provides an apparatus for analyzing particles by emitting a strobe light to a sample flow in an extremely flattened flow condition, having a sheath liquid as an outer layer to obtain a still picture, and analyzing components in the sample liquid by image processing, the apparatus comprises:

an aperture iris disposed before a flow cell, variable means for varying the opening area of the aperture iris, projection lenses differing in scale factor, being disposed after the flow cell and before image pickup means, and means for changing over the projection lenses, being composed so as to possess, in a same sample, either the low scale factor taking state for simultaneously selecting the states of (a), (c), and (e), that is, (a) the state of reducing the quantity of light emitted to the region where the sample liquid flows, (c) the state of passing the sample liquid by increasing its thickness, and (e) the state of taking the still picture of the sample liquid at a low scale factor, or the high scale factor taking state for simultaneously selecting the states of (b), (d), and (f), that is, (b) the state of increasing the quantity of light, (d) the state of passing by reducing the thickness, and (f) the state of taking the picture at a high scale factor:

sheath liquid supply means for supplying a sheath liquid at a specific pressure, sample liquid discharge means capable of controlling the discharge flow rate, a temperature sensor for detecting the ambient temperature, a temperature measuring circuit for measuring the temperature on the basis of the changes of the temperature sensor, and a driving circuit for driving the sample liquid discharge means by correcting the discharge flow rate of the sample liquid discharge means depending on the signal from the temperature measuring circuit, wherein the correction factor is changed whether in the high scale factor taking state or in the low scale factor taking state when correcting the sample liquid discharge flow rate depending on the ambient temperature.

The ambient temperature is measured by the temperature sensor and the temperature measuring circuit, and the temperature information is sent to the driving circuit. In the driving circuit, from the obtained temperature information and the preset data, the operating speed of the sample liquid discharge means is determined. From the sample liquid discharge means, the sample liquid is discharged at a flow rate corresponding to the ambient temperature. That is, at a low temperature, the flow rate of the sample liquid is small, and at a high temperature it is large, so that the flow rates of the sheath liquid and sample liquid are always constantly balanced regardless of the temperature, and hence the width and thickness of the sample liquid are always the same. Hence, the number of photographed particles is also constant.

When photographing by varying in the process the scale factor, depending on the data for a low scale factor and the data for a high scale factor, the discharge volume of the sample liquid is optimally corrected individually, so that the number of photographed particles is always the same whether taken at a high scale factor or at a low scale factor.

DETAILED DESCRIPTION OF THE PREFERRED EMBODIMENTS

Figure 1:
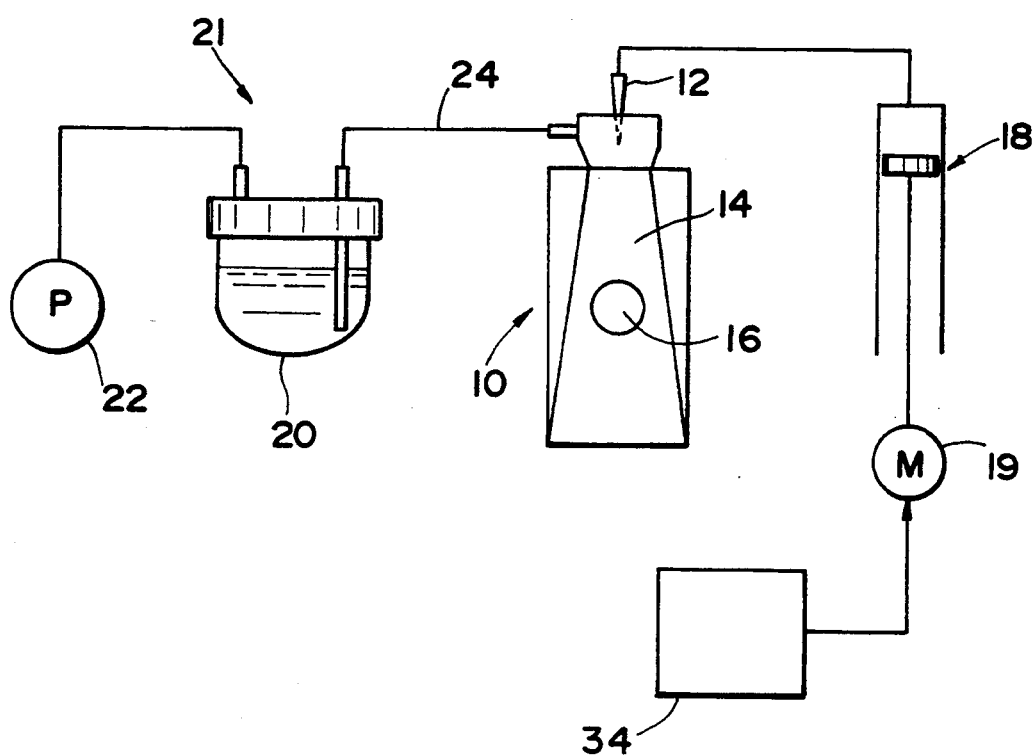
FIG. 1 is a block diagram showing an example of a conventional apparatus for analyzing particles.
Figure 2:
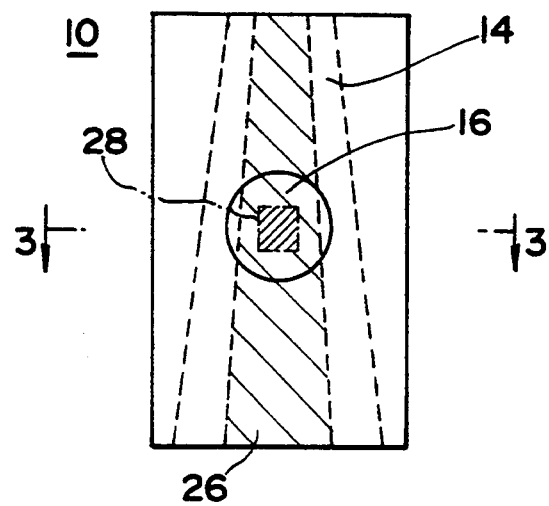
FIG. 2 is an explanatory diagram showing the low temperature state for explaining the flow of sample liquid in a flat sheath flow cell.
Figure 3:
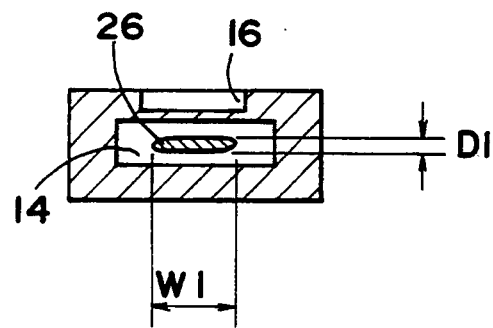
FIG. 3 is a sectional view taken along the line 3—3 in FIG. 2.
Figure 4:
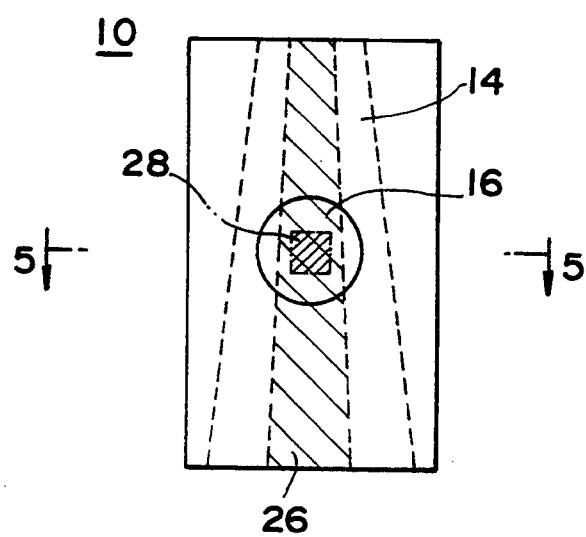
FIG. 4 is an explanatory diagram showing the high temperature state for explaining the flow of sample liquid in a flat sheath flow cell.
Figure 5:
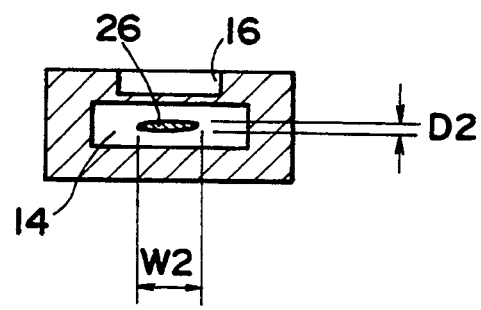
FIG. 5 is a sectional view taken along the line 5—5 in FIG. 4.

Referring now to the drawings, some of the preferred embodiments of the invention are described in detail below.

Figure 8:
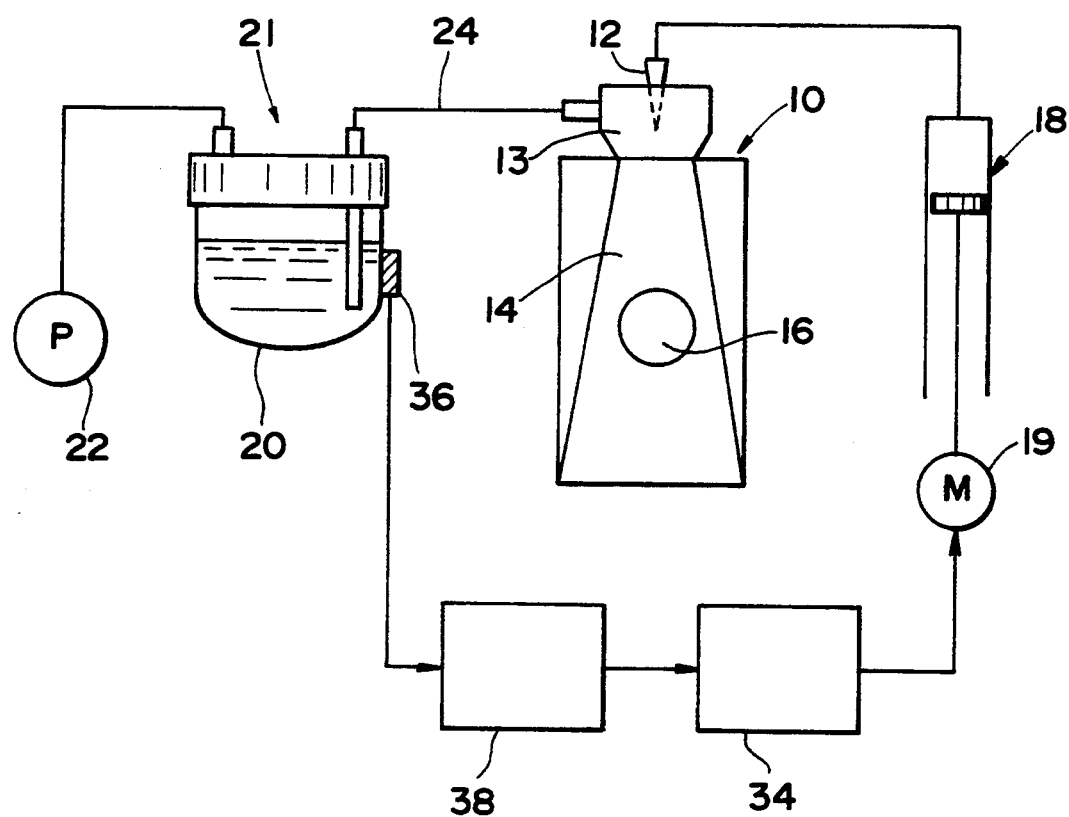
FIG. 8 is a block diagram showing an embodiment of an apparatus for analyzing particles according to the invention.

In FIG. 8, numeral 36 is a temperature sensor for detecting the temperature of a sheath liquid, being mounted on the outer wall of a sheath liquid chamber 20. The temperature sensor 36 is sufficient, if the temperature of the sheath liquid itself is not to be detected, as far as the temperature of a point corresponding to the temperature of the sheath liquid can be detected.

The signal from the temperature sensor 36 is amplified by a temperature measuring circuit 38. As the case may be, the signal may be A/D converted. A signal containing temperature information is sent from the temperature measuring circuit 38 to a driving circuit 34. Numeral 14 is a rectangular passage (flattened passage), and a reducing passage 13 is connected to its upper part.

The sample liquid discharge means 18 is, for example, of a syringe type according to which movement of the piston is achieved by converting the norma and reverse rotary motion of the motor 19 into a reciprocal linear motion. By a drive signal from the driving circuit 34, the discharge flow rate and the suction flow rate of the discharge means 18 may be set to desired values. The flow rate and rotating speed of the motor 19 are in proportional relation. Numeral 21 is a sheath liquid supply means, being composed of a sheath liquid chamber 20, a pump 22, sheath liquid piping 24 and others.

Figure 6:
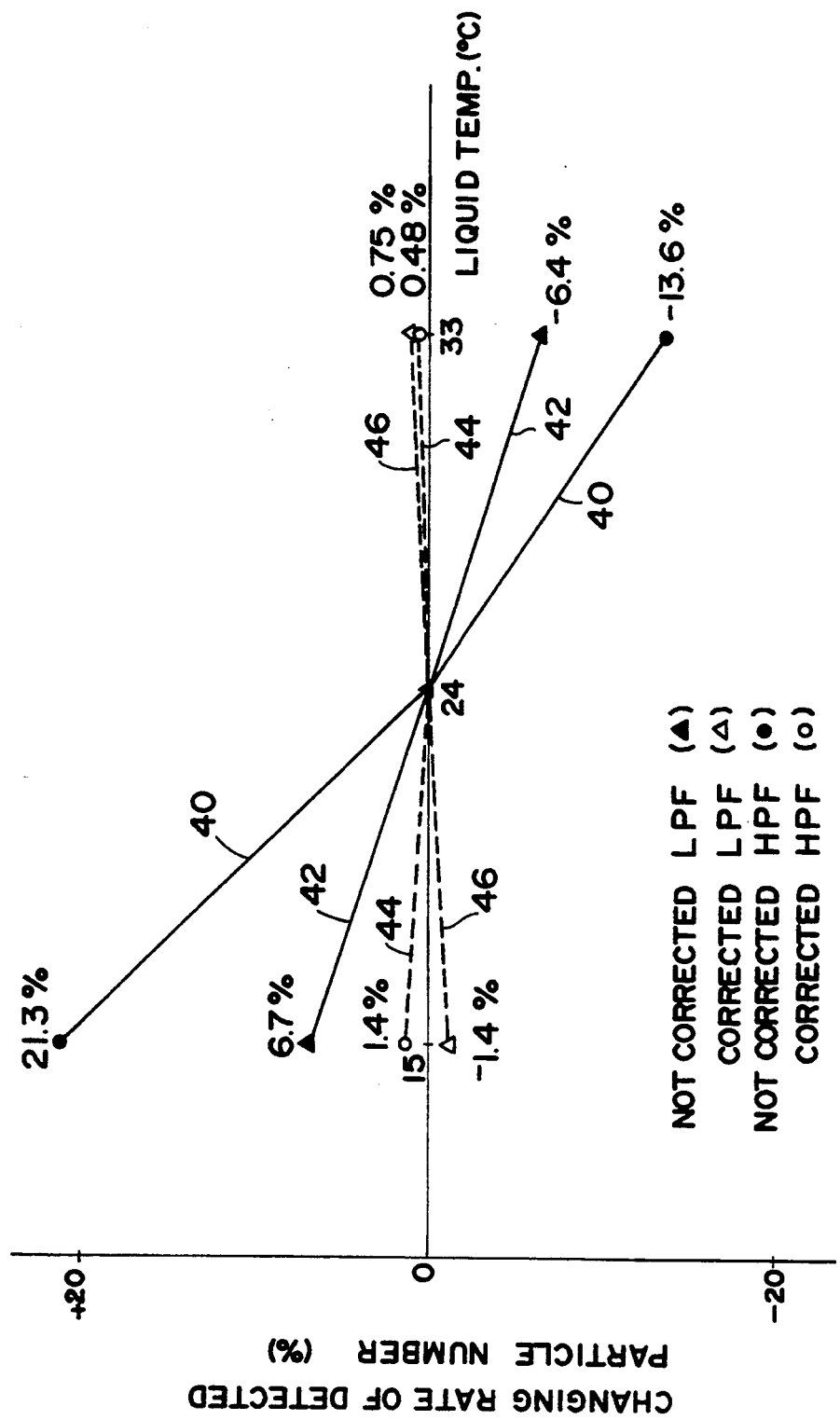
FIG. 6 is a graph showing the relationship between the liquid temperature and the changing rate of particle number detection.
Figure 7:
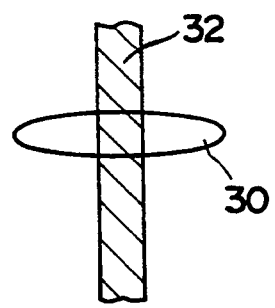
FIG. 7 is a explanatory diagram showing the relationship between the sample liquid flow and the emitted light in an ordinary flow cytometer.

In FIG. 6, when not corrected at all as indicated by solid lines 40, 42, when the liquid temperature varies, the number of detected particles is changed. The lines 40, 42 represent the changes of the number in detected particles in the high scale factor image (HPF) and the low scale factor image (LPF), respectively.

There is, however, a specific relationship between the number of detected particles and the sample liquid discharge flow rate. Accordingly, when the relationship between each number of detected particles and temperature is disclosed by the solid lines 40, 42 in FIG. 6, it is now necessary to determine how fast the motor 19 of the sample liquid discharge means 18 should be rotated in order to keep constant the number of detected particles regardless of the temperature at each scale factor. That is, the correspondence of the temperature and the correction amount of the rotating speed of the motor can be obtained. This correspondence data is stored in the driving circuit 34. By a signal from the temperature measuring circuit 38, the motor 19 rotates at a speed corresponding to the measured temperature, and the sample liquid discharge means 18 also discharges the sample liquid at a discharge flow rate corresponding to the temperature. Or, by installing a circuit for data processing between the temperature measuring circuit 38 and the motor driving circuit 34, the arithmetic operation may be done in this circuit.

More specifically, the rotating speed of the sample liquid discharge means 18 is determined in the following formula, Rotating speed at low scale factor:

$$Q_L(t) = Q_{L24} \times [1 + 7.32 \times 10^{-3} \times (t-24) + 2.85 \times 10^{-5} \times (t-24)^2]$$

Rotating speed at high scale factor:

$$Q_H(t) = Q_{L24} \times [1 + 1.86 \times 10^{-2} \times (t-24) + 5.05 \times 10^{-4} \times (t-24)^2]$$

where, t: is the ambient temperature [°C.]

$Q_{L24}$: is the rotating speed at 24° C. (at low scale factor) and $Q_{H24}$: is the rotating speed at 24° C. (at high scale factor)

Incidentally, the correspondence data may be also obtained by measuring the volume of the sheath liquid flowing within a specific time while varying the temperature, and determining the relationship between the temperature and sheath liquid flow rate.

Thus by correcting and varying the rotating speed of the motor 19; depending on the temperature, the number of detected particles may be kept constant, regardless of the temperature, whether at high scale factor or at low scale factor. Broken lines 44, 46 in FIG. 6 represent fluctuations of the detected particles at high scale factor and low scale factor in corrected cases, respectively.

The changeover of the photographic scale factor is explained below by reference to FIG. 9. The single-dot chain line denotes the optical axis.

Numeral 50 is a strobe, which emits light, for example, for about 5 μs in every 1/30 second. The light from the strobe 50 is focused by collector lens 52. It is further transformed into parallel light by a field lens 54, is reflected nearly 90 degrees by a mirror 56, and enters an aperture iris 58. In this embodiment, between the collector lens 52 and the field lens 54, a diffuser plate 56 and its moving means 57 are provided. The diffuser plate 56 is, for example, a ground glass, and it is supported by a holder 60. The holder 60 is mounted on a rotatable shaft 64 of rotary actuator 62, or motor, or the like, and as the shaft 64 rotates, the pulse light from the strobe 50 passes through the diffuser plate 56 in one state, and does not pass in the other state. By passing through the diffuser plate 56, the light is diffused, and unevenness of luminous intensity is canceled to form a uniform light. As the aperture iris 58 is rotated about the shaft, the area of the light passing the opening varies, so that the quantity of light may be regulated. The aperture iris 58 is rotated by variable means 66, and the area of the opening is changed. The variable means 66 is formed by, for example, attaching a toothed pulley 70 on a rotatable shaft of motor 68 or the like, fitting also a toothed pulley 72 to the outer circumference of the aperture iris 58, and applying a timing belt 74 on both toothed pulleys 72, 70. The light passing through the opening of the aperture iris 58 is focused by a condenser lens 76 to illuminate the small region in which the sample liquid of the flattened passage 80 of the flow cell 78 flows. As the aperture iris 58 is throttled, the quantity of light becomes smaller, and the depth of focus increases. The light passing through the flow cell 78 is magnified, for example, by an objective lens 82 of 10 times magnification, and is reflected by a mirror 84 to pass through projection lens 86 or 88 so as to be taken by image pickup means 90 of a video camera or the like. The projection lenses 86, 88 magnify, for example, by 1 and 4. The projection lenses 86, 88 are supported by a holder 92, and the holder 92 is reciprocally and linearly moved by changeover means 94. The changeover means 94 is realized, for example, by fitting a piston 98 of an air cylinder 96 to the holder 92. To move the holder 92 without excessive play, a linear slider is used. When the projection lens 86 is selected, for example, the scale factor is 10 times in total, and the light passing through the lens 86 directly enters the image pickup means 90 to focus an image on the pickup plane. When the projection lens 88 is selected, the scale factor is, for example, 40 times in total, and the light passing through the lens 88 is reflected by reflection mirrors 100, 102, 104, 106, and enters the image pickup means 90, lengthening optical paths, to focus an image on the pickup plane. It is necessary to cover the optical path from the objective lens 82 to the image pickup means 90 so as to be protected from the effects of disturbance light.

Figure 10:
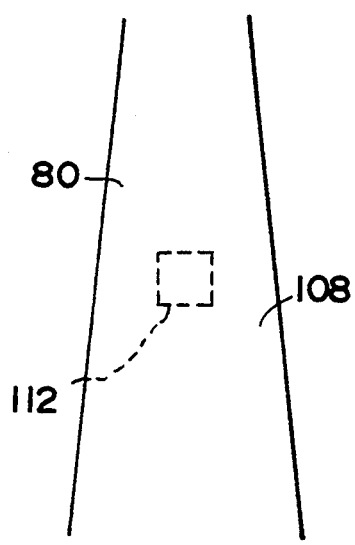
FIG. 10 is an explanatory diagram showing an example of a flattened flow of sample liquid.
Figure 11:
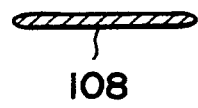
FIG. 11 is a sectional view of the flattened sample liquid in FIG. 10.
Figure 12:
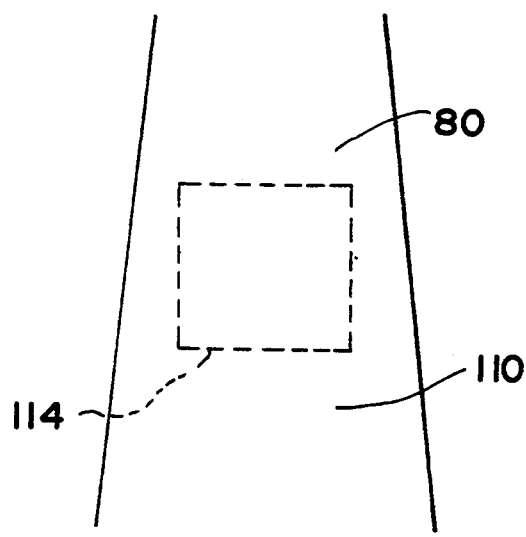
FIG. 12 is an explanatory diagram showing another example of a flattened flow of sample liquid.
Figure 13:
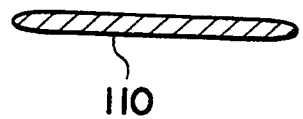
FIG. 13 is a sectional view of the flattened sample liquid in FIG. 12.

FIGS. 10 to 13 are diagrams showing liquid samples 108, 110 flowing in the central part of the flattened passage 80 of the flow cell 78. FIGS. 11 and 13 are sectional views of liquid samples 108, 110. In FIGS. 10 and 12, numerals 112 and 114 indicate the viewing field (pickup area) at the scale factors of, for example, 40 times and 10 times, respectively. The optical system is designed so that 0.61 NA/$\lambda$ and 2× pixel interval/M may be approximately equal to each other at a high scale factor, where NA is the number of openings of the lens, $\lambda$ is the light wavelength, and M is the scale factor of the lens. At 40 times, the object field depth is relatively shallow. Accordingly, as shown in FIG. 11, it is necessary to prepare the thickness of the sample liquid flow slightly less than the object field depth. Besides in order to take a picture of as many particles as possible, it is necessary that the sample liquid be flowing so as to cover the entire region of the viewing field. At 10 times, the object field depth is relatively deep. Accordingly, as shown in FIG. 11, the focus is matched when the thickness of the sample liquid flow is thin. However, for the smallness of the thickness of the sample liquid flow, the photographed sample liquid is smaller, the number of obtained particles is smaller, and the precision of analysis is lowered. A urine sample is very small in the number of particles contained as compared with blood or other samples. Preferably, therefore, the thickness of the sample liquid flow should be slightly less than the object field depth of the lens. When it is desired to lower the scale factor, accordingly, it is desired to pass the sample liquid so that the thickness may be sufficient as shown in FIG. 13.

To vary the thickness of the sample liquid flow, either one or both of the sheath liquid supply volume and sample liquid supply volume should be changed. The structure is simple when it is designed to change only the sample liquid supply volume while fixing the sheath liquid supply volume.

When changing over the lenses, if the lens position is shifted upon every changeover, the lens becomes off focus or the image cannot be picked up correctly. It is therefore necessary to arrange so that such troubles may not occur if the lens position is changed only slightly. It is preferable in this respect to keep the scale factor of the lens to be moved (in this example, the scale factor of the projection lenses is 1 and 4) low. On the other hand, the scale factor of the fixed objective lens 82 is set larger (10 times in the objective lens in this example).

Figure 9:
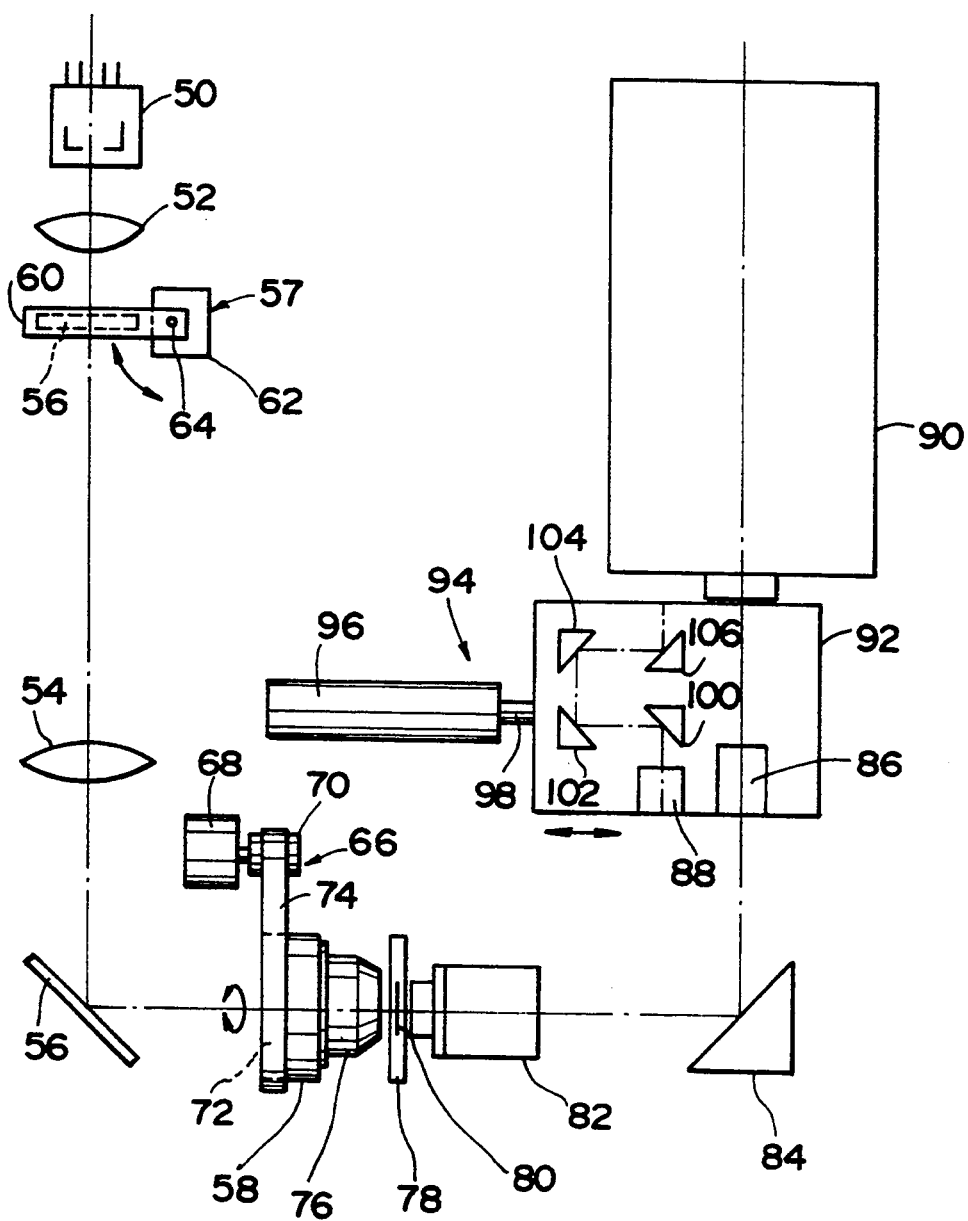
FIG. 9 is a block diagram for explaining the changeover of photographic scale factors according to the invention.

In the apparatus shown in FIG. 9, when photographing the sample liquid at a low scale factor, the object field depth of the lens is deep. Therefore, the focus can be adjusted within the range if the thickness of the sample liquid flow is great. At a low scale factor, the region of photographing the sample flow, that is, the viewing field is wide. Hence, a sufficient light signal reaches the image pickup means, and a bright image is obtained if the quantity of illuminating light is small.

When photographing the sample liquid at a high scale factor, the object field depth of the lens is shallow. Therefore, unless the thickness of the sample flow is reduced, off-focus parts are caused and the thickness of the sample flow is reduced. At a high scale factor, the viewing field is narrow. When the quantity of illuminating light is the same as at a low scale factor, the quantity of light reaching the pickup means is smaller. Accordingly, in the case of a high scale factor, the quantity of illuminating light is increased as compared with the case of a low scale factor so that nearly the same quantity of light may reach the image pickup means.

Thus, whether at a low scale factor or at a high scale factor, a focused, sharp image without change in brightness is obtained.

If the intensity of the illuminating light is uneven in the pickup viewing field, the intensity may be made uniform by diffusing light. By emitting the uniform light to the sample flow, an image of uniform background will be obtained. The unevenness of luminous intensity is possible to appear within the viewing field when the viewing field is wide and the scale factor is low.

Blood corpuscles and epithelial cells are easily dyed by dyestuff. On the other hand, the cylinders are larger than small epithelial cells, crystals, leukocytes and bacteria, and are hardly dyed. Accordingly, in the first place, at a high scale factor, relatively small blood corpuscles and epithelials are photographed, then at a low factor, relatively large cylinders, squamous epithelium, leukocyte clots and others are targeted, so that the dyeing time of cylinders and others may be extended, if only slightly, thereby obtaining well dyed cylinders.

Besides, the flow rate ratio of the sample liquid and sheath liquid may be varied by changing the feed amount of the sample liquid without changing the feed amount of the sheath liquid, so that the volume of the sample liquid flowing in a flat sheath flow may be varied.

Moreover, in the apparatus shown in FIG. 9, the sample liquid is forced out from the tip of the nozzle by the sample liquid supply means, and flows through a reducing passage (numeral 13 in FIG. 8) of the flow cell 78. On the other hand, sheath liquid is supplied from the sheath liquid supply means into the reducing passage of the flow cell 78. The sample liquid is surrounded with sheath liquid, and flows through the reducing passage of the flow cell 78 and the communicating flattened passage 80 (numeral 14 in FIG. 8). The flattened passage 80 is smaller in thickness as compared with the width, and the sample follows the shape of this flattened passage 80 to be formed into an extremely flattened flow smaller in thickness as compared with the width.

The light of a short emission time is continuously emitted from the strobe 50. This light passes through the aperture iris 58. The aperture iris 58 is varied in the opening area by the variable means 66, and the quantity of passing light is changed. The light passing through the aperture iris 58 is converged by a condenser lens 76, and is emitted to the measuring area in which the sample liquid of the flattened passage 80 flows. The light passing through the flattened passage 80 of the flow cell 78 is magnified to a specific factor by the objective lens 82, projection lesses 86 or 88, and is picked up by the image pickup means 90. The projection lenses 86, 88 are held by the holder 92, and this holder 92 is moved by the changeover means 94, thereby changing over the projection lenses. By properly selecting the sample feed speed by the sample supply means, the opening area of the aperture iris 58 by the variable means 66, and the projection lenses 86 or 88 by the changeover means 94, and synchronizing, the state of the low scale factor and the state of the high scale factor may be produced.

Besides, by the moving means 57, the state of disposing the diffuser plate 56 and the state of not disposing between the strobe 59 and aperture iris 58 may be produced.

Being thus constructed, the invention brings about the following effects.

(1) In the method and apparatus for analyzing only a part of the sample liquid by feeding the sheath liquid at a specific pressure, the sample discharge flow rate is corrected and varied depending on the temperature, and the thickness and width of the sample liquid may be kept constant if the ambient temperature fluctuates. Hence, the number of detected particles is unchanged and the precision of analysis may be kept constant.

(2) Compared with the method (a) or (b) disclosed the prior art, the cost is lower and the size is smaller.

(3) When changing over the scale factor in the midst of measuring, the correction amount of the sample liquid discharge flow rate is changed whether at a low scale factor or at a high scale factor, and anyway, regardless of the temperature, a specific number of particles may always be detected.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for analyzing particles in a sample liquid by emitting a strobe light to a sample liquid flow in an extremely flattened flow condition, having a sheath liquid as an outer layer to obtain a still picture, and analyzing components in the sample liquid by image processing, comprising:

a flow cell for producing a flow of a sample liquid containing particles, the flow of the sample liquid being surrounded by a flow of sheath liquid from the sheath liquid supply means;

a light source for emitting light to the sample liquid flow;

image pick up means for picking up the image of the particles produced by the light from the sample flow;

an image processor for processing the image pick up;

an aperture iris disposed on the upstream side of the flow cell;

variable means for varying the opening area of the aperture iris;

projection lenses differing in scale factor, being disposed on the downstream side of the flow cell and on the upstream side of the image pickup means;

means for changing over the projection lenses, said means for changing including at least the following states: the low scale factor taking state for simultaneously selecting the state of reducing the quantity of light emitted to the region where the sample liquid flows, the state of passing the sample liquid by increasing its thickness, and the state of taking the still picture of the sample liquid at a low scale factor, and the high scale factor taking state of simultaneously selecting the state of increasing the quantity of light, the state of passing by reducing the thickness, and the state of taking the picture at a high scale factor;

sheath liquid supply means for supplying a sheath liquid at a specific pressure;

sample liquid discharge means capable of controlling the discharge flow rate;

a temperature sensor for detecting the ambient temperature;

a temperature measuring circuit for measuring the temperature on the basis of the output of the temperature sensor; and a driving circuit for driving the sample liquid discharge means and correcting the discharge flow rate of the sample liquid discharge means by the signal from the temperature measuring circuit, wherein the correction factor is changed whether in the high scale factor taking state or in the low scale factor taking state when correcting the sample liquid discharge flow rate depending on the ambient temperature.

2. The apparatus according to claim 1, further wherein the driving circuit stores the correspondence data between the ambient temperature and the sample liquid discharge flow rate of the sample liquid discharge means in the ambient temperature, and the sample liquid discharge means is driven so that the sample liquid discharge flow rate is equal to the sample discharge flow rate corresponding to the measured temperature.

* * * * *